United States Patent [19]

Ohtuka et al.

[11] Patent Number: 4,608,438

[45] Date of Patent: Aug. 26, 1986

[54] IMIDAZOLE DERIVATIVES

[75] Inventors: Katuyuki Ohtuka, Nagareyama; Kazuya Sasaki, Higashi-Kurume; Tadashi Arika, Kasukabe; Mamoru Yokoo, Kawagoe; Kouji Amemiya, Kodaira, all of Japan

[73] Assignee: Kaken Pharmaceutical Co., Ltd., Tokyo, Japan

[21] Appl. No.: 641,198

[22] Filed: Aug. 16, 1984

[30] Foreign Application Priority Data

Sep. 13, 1983 [JP] Japan ................................. 58-167560

[51] Int. Cl.$^4$ ................ C07D 233/60; C07D 409/06; C07D 405/06
[52] U.S. Cl. .................................... 548/341; 548/336
[58] Field of Search .............................. 548/341, 336

[56] References Cited

U.S. PATENT DOCUMENTS

| | | | |
|---|---|---|---|
| 3,755,349 | 8/1973 | Timmler et al. | 548/341 |
| 4,235,620 | 11/1980 | Lewis et al. | 548/341 X |
| 4,246,020 | 1/1981 | Shepard et al. | 548/341 X |
| 4,273,776 | 6/1981 | Hoehn | 548/341 X |

Primary Examiner—Richard A. Schwartz

Attorney, Agent, or Firm—Oblon, Fisher, Spivak, McClelland & Maier

[57] ABSTRACT

An antifungal and antibacterial imidazole derivative represented by the general formula I or a biologically acceptable acid addition salt thereof:

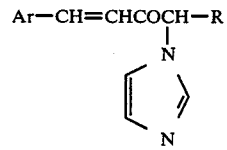

where Ar is a phenyl group which may be substituted by alkyl having from 1 to 6 carbon atoms, alkoxy having from 1 to 4 carbon atoms, alkylamino having from 1 to 4 carbon atoms, alkoxy carbonyl having from 1 to 4 carbon atoms, phenyl, halogen or hydroxyl; a naphthyl group; a furyl group; or a thienyl group which may be substituted by halogen or alkyl having from 1 to 4 carbon atoms, and R is an alkyl group having from 1 to 10 carbon atoms; an alkenyl group having from 1 to 6 carbon atoms; or a phenylalkyl group which may be substituted by halogen.

7 Claims, No Drawings

IMIDAZOLE DERIVATIVES

The present invention relates to novel imidazole derivatives and their biologically acceptable acid addition salts, and processes for the production thereof.

Namely, the present invention provides an imidazole derivative represented by the general formula I or a biologically acceptable acid addition salt thereof:

$$Ar-CH=CHCOCH(-N\text{-imidazole})-R \quad (I)$$

where Ar is a phenyl group which may be substituted by alkyl having from 1 to 6 carbon atoms, alkoxy having from 1 to 4 carbon atoms, alkylamino having from 1 to 4 carbon atoms, alkoxy carbonyl having from 1 to 4 carbon atoms, phenyl, halogen or hydroxyl; a naphthyl group; a furyl group; or a thienyl group which may be substituted by halogen or alkyl having from 1 to 4 carbon atoms, and R is an alkyl group having from 1 to 10 carbon atoms; an alkenyl group having from 1 to 6 carbon atoms; or a phenylalkyl group which may be substituted by halogen.

The novel imidazole derivatives and their biologically acceptable acid addition salts exhibit antifungal and antibacterial activities.

The imidazole derivative of the general formula I may be prepared by reacting a compound represented by the general formula II:

$$Ar-CH=CHCO-CH(X)-R \quad (II)$$

where X is a halogen atom and Ar and R are as defined above, with imidazole, or by reacting a compound represented by the general formula III:

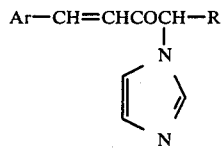

where R is as defined above, with a compound represented by the general formula (IV):

$$Ar-CHO \quad (IV)$$

where Ar is as defined above. The imidazole derivative of the formula I thus prepared, may optionally be converted to its biologically acceptable acid addition salt.

Now, the present invention will be described in detail with reference to the preferred embodiments.

In the general formula I, Ar is an unsubstituted phenyl group; a phenyl group substituted by $C_1-C_6$ alkyl such as methyl, ethyl, propyl, butyl, pentyl or hexyl, $C_1-C_4$ alkoxy such as methoxy, ethoxy, propoxy or butoxy, $C_1-C_4$ alkylamino such as methylamino, ethylamino, propylamino or butylamino, $C_1-C_4$ alkoxy carbonyl such as methylcarbonyl, ethylcarbonyl, propylcarbonyl or butylcarbonyl, phenyl, halogen such as fluorine, chlorine, bromine or iodine, or hydroxyl; a phenyl group; a naphthyl group; a furyl group; or an unsubstituted thienyl group; or a thienyl group substituted by halogen such as fluorine, chlorine, bromine or iodine, or $C_1-C_4$ alkyl such as methyl, ethyl, propyl or butyl. Specific examples of Ar include

[structures of substituted phenyl, naphthyl, thienyl and furyl groups]

Likewise, in the general formula I, R is a $C_1-C_{10}$ alkyl group such as methyl, ethyl, propyl, isopropyl, butyl, isobutyl, pentyl, hexyl, heptyl or octyl; a $C_1-C_6$ alkenyl group such as allyl, butenyl, 3-methyl-butenyl or pentenyl; or a phenylalkyl group such as phenylmethyl or phenylethyl, which may be substituted by halogen such as fluorine, chlorine, bromine or iodine. Specific examples of R include $-CH_2CH_3$, $-(CH_2)_2CH_3$, $-(CH_2)_3CH_3$, $-(CH_2)_4CH_3$, $-(CH_2)_5CH_3$, $-(CH_2)_6CH_3$, $-(CH_2)_7CH_3$, $-CH(CH_3)_2$, $-CH_2CH(CH_3)_2$, $-CH_2CH=CH_2$, $-CH_2CH=CHCH_3$, $-CH_2CH=C(CH_3)_2$, $-CH_2-\text{C}_6H_4\text{Cl}$, $-CH_2-\text{C}_6H_3\text{Cl}_2$ and $-CH_2CH_2-\text{C}_6H_5$.

Most of the free bases of the imidazole derivatives of the formula I are oily, but they may be converted to their biologically acceptable acid addition salts and thus can be isolated in the form of crystals. There is no particular restriction to the biologically acceptable acid addition salts so long as they are biologically acceptable. As the acid to form the biologically acceptable acid addition salt, there may be employed an inorganic acid such as hydrochloric acid, hydrobromic acid, nitric acid, sulfuric acid or phosphoric acid, or an organic acid such as acetic acid, propionic acid, glycolic acid, lactic acid, oxalic acid, malonic acid, fumaric acid, tartaric acid, citric acid, maleic acid, malic acid, benzoic acid, cinnamic acid, mandelic acid, methanesulfonic acid, ethanesulfonic acid or p-toluenesulfonic acid.

As specific examples of the imidazole derivatives of the formula I, there may be mentioned the following compounds:

1-(4'-chlorophenyl)-4-(imidazole-1''-yl)-1-hexene-3-one,
1-(4'-chlorophenyl)-4-(imidazoel-1''-yl)-1-heptene-3-one,
1-(4'-chlorophenyl)-4-(imidazole-1''-yl)-1-octene-3-one,
1-(4'-chlorophenyl)-4-(imidazole-1''-yl)-1-nonene-3-one,
1-(4'-chlorophenyl)-4-(imidazole-1''-yl)-1-decene-3-one,
1-(4'-chlorophenyl)-4-(imidazole-1''-yl)-1-undecene-3-one,
1-(4'-chlorophenyl)-4-(imidazole-1''-yl)-1-dodecene-3-one,
1-(4'-chlorophenyl)-4-(imidazole-1''-yl)-5-methyl-1-hexene-3-one,
1-(4'-chlorophenyl)-4-(imidazole-1''-yl)-6-methyl-1-heptene-3-one,
1-(4'-chlorophenyl)-4-(imidazole-1''-yl)-1,6-heptadiene-3-one,
1-(4'-chlorophenyl)-4-(imidazole-1''-yl)-7-methyl-1,6-octadiene-3-one,
1-(4'-chlorophenyl)-4-(imidazole-1''-yl)-5-phenyl-1-pentene-3-one,
1-(4'-chlorophenyl)-4-(imidazole-1''-yl)-5-(2'-chlorophenyl)-1-pentene-3-one,
1-(4'-chlorophenyl)-4-(imidazole-1''-yl)-5-(4'-chlorophenyl-1-pentene-3-one,
1-(4'-chlorophenyl)-4-(imidazole-1''-yl)-5-(2',4'-dichlorophenyl)-1-pentene-3-one,
1-(4'-chlorophenyl)-4-(imidazole-1''-yl)-5-(3',4'-dichlorophenyl)-1-pentene-3-one,
1-(4'-chlorophenyl)-4-(imidazole-1''-yl)-6-phenyl-1-hexene-3-one,
1-(2'-methylphenyl)-4-(imidazole-1''-yl)-1-heptene-3-one,
1-(2'-methylphenyl)-4-(imidazole-1''-yl)-1-octene-3-one,
1-(2'-methylphenyl)-4-(imidazole-1''-yl)-1-nonene-3-one,
1-(2'-methylphenyl)-4-(imidazole-1''-yl)-6-methyl-1-heptene-3-one,
1-(3'-methylphenyl)-4-(imidazole-1''-yl)-1-heptene-3-one,
1-(3'-methylphenyl)-4-(imidazole-1''-yl)-1-octene-3-one,
1-(3'-methylphenyl)-4-(imidazole-1''-yl)-1-nonene-3-one,
1-(3'-methylphenyl)-4-(imidazole-1''-yl)-6-methyl-1-heptene-3-one,
1-(4'-methylphenyl)-4-(imidazole-1''-yl)-1-heptene-3-one,
1-(4'-methylphenyl)-4-(imidazole-1''-yl)-1-octene-3-one,
1-(4'-methylphenyl)-4-(imidazole-1''-yl)-1-nonene-3-one,
1-(4'-methylphenyl)-4-(imidazole-1''-yl)-6-methyl-1-heptene-3-one,
1-phenyl-4-(imidazole-1'-yl)-1-octene-3-one,
1-phenyl-4-(imidazole-1'-yl)-1-nonene-3-one,
1-(4'-methoxyphenyl)-4-(imidazole-1''-yl)-1-octene-3-one,
1-(4'-methoxyphenyl)-4-(imidazole-1''-yl)-1-nonene-3-one,
1-(3'-methoxyphenyl)-4-(imidazole-1''-yl)-1-octene-3-one,
1-(3'-methoxyphenyl)-4-(imidazole-1''-yl)-1-nonene-3-one,
1-(2'-methoxyphenyl)-4-(imidazole-1''-yl)-1-octene-3-one,
1-(2'-methoxyphenyl)-4-(imidazole-1''-yl)-1-nonene-3-one,
1-(3',4'-dimethoxyphenyl)-4-(imidazole-1''-yl)-1-octene-3-one,
1-(3',4'-dimethoxyphenyl)-4-(imidazole-1''-yl)-1-nonene-3-one,
1-(2',5'-dimethoxyphenyl)-4-(imidazole-1''-yl)-1-octene-3-one,
1-(2',5'-dimethoxyphenyl)-4-(imidazole-1''-yl)-1-nonene-3-one,
1-(2',3'-dimethoxyphenyl)-4-(imidazole-1''-yl)-1-octene-3-one,
1-(2',3'-dimethoxyphenyl)-4-(imidazole-1''-yl)-1-nonene-3-one,
1-(2',4'-dimethoxyphenyl)-4-(imidazole-1''-yl)-octene-3-one,
1-(2',4'-dimethoxyphenyl)-4-(imidazole-1''-yl)-1-nonene-3-one,
1-(1-naphthyl)-4-(imidazole-1''-yl)-1-octene-3-one,
1-(1-naphthyl)-4-(imidazole-1''-yl)-1-nonene-3-one,
1-(2-thienyl)-4-(imidazole-1''-yl)-1-octene-3-one,
1-(2-thienyl)-4-(imidazole-1''-yl)-1-nonene-3-one,
1-(3'-methyl-2'-thienyl)-4-(imidazole-1''-yl)-1-octene-3-one,
1-(3'-methyl-2'-thienyl)-4-(imidazole-1-yl)-1-nonene-3-one,
1-(5'-methyl-2'-thienyl)-4-imidazole-1-yl)-1-octene-3-one,
1-(5'-methyl-2'-thienyl)-4-(imidazole-1-yl)-1-nonene-3-one,
1-(5'-chloro-2'-thienyl)-4-(imidazole-1''-yl)-1-octene-3-one
1-(2'-furyl)-4-(imidazole-1''-yl)-1-octene-3-one,
1-(2'-furyl)-4-(imidazole-1''-yl)-1-nonene-3-one,
1-(2'-chlorophenyl)-4-(imidazole-1''-yl)-1-octene-3-one,
1-(2'-chlorophenyl)-4-(imidazole-1-yl)-1-nonene-3-one,
1-(3'-chlorophenyl)-4-(imidazole-1''-yl)-1-nonene-3-one,
1-(2',6'-dichlorophenyl)-4-(imidazole-1''-yl)-1-octene-3-one,
1-(2',6'-dichlorophenyl)-4-(imidazole-1''-yl)-1-nonene-3-one,
1-(2',4'-dichlorophenyl)-4-(imidazole-1''-yl)-1-octene-3-one,
1-(2',4'-dichlorophenyl)-4-(imidazole-1''-yl)-1-nonene-3-one,
1-(3',4'-dichlorophenyl)-4-(imidazole-1''-yl)-1-octene-3-one,
1-(3',4'-dichlorophenyl)-4-(imidazole-1''-yl)-1-nonene-3-one,
1-(4'-fluorophenyl)-4-(imidazole-1''-yl)-1-octene-3-one,
1-(4'-fluorophenyl)-4-(imidazole-1-yl)-1-nonene-3-one,
1-(4'-dimethylaminophenyl)-4-(imidazole-1''-yl)-1-octene-3-one,
1-(4'-dimethylaminophenyl)-4-(imidazole-1''-yl)-1-nonene-3-one,
1-(4'-bromophenyl)-4-(imidazole-1''-yl)-1-octene-3-one,
1-(4'-bromophenyl)-4-(imidazole-1''-yl)-1-nonene-3-one,
1-(4'-methoxycarbonylphenyl)-4-(imidazole-1''-yl)-1-octene-3-one,
1-(4'-methoxycarbonylphenyl)-4-(imidazole-1''-yl)-1-nonene-3-one, 1-(3'-methoxycarbonylphenyl)-4-(imidazole-1"-yl)-1-octene-3-one,
1-(3'-methoxycarbonylphenyl)-4-(imidazole-1"-yl)-1-nonene-3-one,
1-(4'-butylphenyl)-4-(imidazole-1"-yl)-1-octene-3-one,
1-(4'-butylphenyl)-4-(imidazole-1"-yl)-1-nonene-3-one,
1-(4'-sec-butylphenyl)-4-(imidazole-1"-yl)-1-octene-3-one,
1-(4'-sec-butylphenyl)-4-(imidazole-1"-yl)-1-none-3-one,
1-(4'-tert-butylphenyl)-4-(imidazole-1"-yl)-1-octene-3-one,
1-(4'-tert-butylphenyl)-4-(imidazole-1"-yl)-1-nonene-3-one,
1-(4'-biphenylyl)-4-(imidazole-1"-yl)-1-octene-3-one,
1-(4'-biphenylyl)-4-(imidazole-1"-yl)-1-nonene-3-one,
1-(4'-hydroxyphenyl)-4-(imidazole-1"-yl)-1-octene-3-one,
1-(4'-hydroxyphenyl)-4-(imidazole-1"-yl)-1-nonene-3-one,
1-(3'-hdyroxyphenyl)-4-(imidazole-1"-yl)-1-octene-3-one,
1-(2'-hydroxyphenyl)-4-(imidazole-1"-yl)-1-octene-3-one,
1-(3',4'-dihydroxyphenyl)-4-(imidazole-1"-yl)-1-octene-3-one,
1-(3',4'-dihydroxyphenyl)-4-(imidazole-1"-yl)-1-nonene-3-one,
1-(3'-methoxy-4'-hydroxyphenyl)-4-(imidazole-1-yl)-1-octene-3-one, and
1-(3'-methoxy-4'-hydroxyphenyl)-4-(imidazole-1-yl)-1-nonene-3-one.

The imidazole derivative of the general formula I may be prepared by reacting the compound of the general formula II with imidazole.

This reaction is preferably conducted in an inert solvent by using from 1 to 5 mols of imidazole relative to 1 mol of the compound of the formula II. As the solvent, there may be employed dimethylformamide, dimethylsulfoxide, dimethylacetoamide or acetonirile. The reaction is conducted at a temperature of from 10° to 100° C. for 30 minutes to 10 hours.

The starting material of the formula II may be prepared by e.g. the following method. Namely, a compound represented by the general formula III':

where R is as defined above, is reacted with a compound of the general formula IV to obtain a compound represented by the general formula V:

where Ar and R are as defined above. This aldol-type condensation reaction may be conducted in accordance with a method disclosed in e.g. Journal of American Chemical Society, Vol. 72, p 1604 (1950). Then, the compound of the formula V is reacted with a copper (II) halide in an inert solvent to obtain a compound of the formula II. As the copper (II) halide, it is preferred to use copper (II) bromide. The amount of the copper (II) halide is about 2 mols relative to 1 mol of the compound of the formula V. As the solvent, there may be used ether, tetrahydrofuran, dimethoxyethane or dioxane. The reaction is preferably conducted at a temperature of from 50° to 100° C.

Alternatively, the imidazole derivative of the formula I may be prepared by reacting a compound of the formula III with a compound of the formula IV.

This reaction is preferably conducted in an inert solvent in the presence of a basic condensing agent. As the solvent, there may be employed a lower alcohol such as methanol, ethanol or propanol. As the basic condensing agent, there may be employed potassium carbonate or sodium carbonate. The reaction is preferably conducted at a temperature of from 0° to 50° C.

The starting material of the formula IV may be prepared by e.g. the following method. Namely, when a compound of the formula III' is halogenated in accordance with the method disclosed in Journal of Chemical Society (1948) p 272, a compound represented by the general formula VI:

where R and X are as defined above, is obtained. Then, the compound of the formula VI is reacted with imidazole in an inert solvent to obtain a compound of the formula III. The amount of imidazole is from 1 to 5 mols relative to 1 mol of the compound of the formula VI. As the solvent, there may be employed dimethylformamide, dimethylsulfoxide or acetonirile. The reaction is conducted at a temperature of from 20° to 100° C.

The imidazole derivatives of the formula I and their biologically acceptable acid addition salts exhibit remarkable antifungal and antibacterial activities against the following microorganisms: *Nocardia asteroides, Candida albicans, Candida tropicalis, Candida pseudotropicalia, Cryptococcus albidus, Cryptococcus neoformans, Rhodotorula glutinis, Torulopsis candia, Torulopsis colliculosa, Trichosporon cutaneum, Geotrichum candidum, Aspergillus fumigatus, Aspergillus candidus, Hormodendrum pedrosoi, Microsporum gypseum, Phialophora verrucosa, Sporothix schenkii, Trichophyton interdigital, Trichophyton rubrum, Trichophyton mentagrophytes,* Saprolegnia and bacteria such as *Staphylococcus aureus.*

Thus, the imidazole derivatives and their biologically acceptable acid addition salts of the present invention are useful as antifungal and antibacterial agents.

Now, the present invention will be described in further detail with reference to Examples. However, it should be understood that the present invention is by no means restricted to these specific Examples.

EXAMPLE 1

(a) 4.3 g of 1-(p-bromophenyl)-1-octene-3-one was dissolved in 400 ml of tetrahydrofuran. To this solution, 8.3 g of copper (II) bromide was added under stirring and stirred at a temperature of from 70° to 80° C. for 2 hours. After cooling the reaction mixture, the precipitated crystals were filtered off, and tetrahydrofuran was distilled off under reduced pressure from the filtrate. The residue was purified by chromatography, whereby 1-(4'-bromophenyl)-4-bromo-1-octene-3-one was obtained as an oily product.

(b) 6.0 g of imidazole was dissolved in 20 ml of N,N-dimethylforamide. While stirring this solution at room temperature, a solution obtained by dissolving 4.0 g of the oily product obtained in (a) in 10 ml of N,N-dimethylformamide, was gradually added. The mixture was stirred at room temperature for 4 hours, and the reaction mixture was poured into water and extracted with chloroform. The extraction solution was treated in a usual manner and purified by chromatography, whereby 1-(4'-bromophenyl)-4-(imidazole-1-yl)-1-octene-3-one was obtained as an oily product.

This oily product was dissolved in 50 ml of ether, and 1 ml of concentrated nitric acid was gradually added thereto. The precipitated crystals were collected by filtration and recrystallized from ethanol, whereby 1-(4'-bromophenyl)-4-(imidazole-1-yl)-1-octene-3-one nitrate was obtained.

Melting point: 122°–123° C.

IR spectrum $\nu_{max cm^{-1}}^{KBr}$: 2960, 2935, 1708, 1610, 1580, 1495.

NMR spectrum (δ ppm 60 Mdz, DMSO-$d_6$): 0.88(t, 3H), 0.9–180(m, 4H), 1.9–2.4 (m,2H),5.78, 5.98(dd, 1H), 7.1–8.0(m, 8H), 9.36(m, 1H).

EXAMPLES 2 TO 34

In the same manner as in Example 1, the following compounds were obtained starting with the corresponding ketones. The solvent used for the measurement of NMR was DMSO-$d_6$.

TABLE 1

| Example No. | Ar | R | Acid addition salt | Melting point (°C.) | $IR_{max}cm^{-1}$ (C=O) | NMR ppm |
|---|---|---|---|---|---|---|
| 2 | 4-Cl-phenyl | —CH₂CH₃ | Nitrate | 129–131 | 1710 (KBr) | 5.65, 5.83 (dd, 1H) |
| 3 | " | —(CH₂)₂CH₃ | " | 134–135 | 1710 (KBr) | 5.89, 6.03 (dd, 1H) |
| 4 | " | —(CH₂)₃CH₃ | " | 116–118 | 1710 (KBr) | 5.80, 5.97 (dd, 1H) |
| 5 | " | —(CH₂)₄CH₃ | " | 131–133 | 1710 (KBr) | 5.78, 5.96 (dd, 1H) |
| 6 | " | —(CH₂)₅CH₃ | " | 119–121 | 1710 (KBr) | 5.78, 5.95 (dd, 1H) |
| 7 | " | —(CH₂)₆CH₃ | " | 97–98 | 1710 (KBr) | 5.75, 5.93 (dd, 1H) |
| 8 | " | —(CH₂)₇CH₃ | " | 101–103 | 1710 (KBr) | 5.80, 5.93 (dd, 1H) |
| 9 | " | —CH(CH₃)₂ | " | 142–144 | 1710 (KBr) | 5.82 (d, 1H) |
| 10 | " | —CH₂CH(CH₃)₂ | " | 131–134 | 1710 (KBr) | 5.01 (t, 1H) |
| 11 | " | —CH₂CH=CH₂ | " | 130–132 | 1710 (KBr) | 5.90, 6.08 (dd, 1H) |
| 12 | " | —CH₂CH=CHCH₃ | " | 119–121 | 1710 (KBr) | 5.76, 5.95 (dd, 1H) |
| 13 | " | —CH₂CH=C(CH₃)₂ | " | 133–134 | 1710 (KBr) | 5.70, 5.88 (dd, 1H) |
| 14 | " | —CH₂-(2-Cl-phenyl) | " | 153–155 | 1710 (KBr) | 6.20, 6.36 (dd, 1H) |
| 15 | " | —CH₂-(4-Cl-phenyl) | " | 154–155 | 1710 (KBr) | 6.15, 6.32 (dd, 1H) |
| 16 | " | —CH₂-(2,4-di-Cl-phenyl) | " | 153–155 | 1710 (KBr) | 6.10, 6.28 (dd, 1H) |

TABLE 1-continued

| Example No. | Ar | R | Acid addition salt | Melting point (°C.) | IR$_{max}$cm$^{-1}$ (C=O) | NMR ppm |
|---|---|---|---|---|---|---|
| 17 | " | 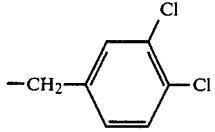 —CH₂— (3,4-dichlorophenyl) | " | 151–152 | 1710 (KBr) | 6.15, 6.33 (dd, 1H) |
| 18 | " | —CH₂CH₂— 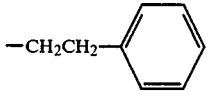 | " | 145–147 | 1710 (KBr) | 5.73, 5.95 (dd, 1H) |
| 19 | 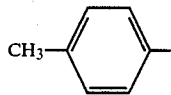 (4-CH₃-phenyl) | —(CH₂)₂CH₃ | " | 137–139 | 1710 (KBr) | 5.83, 6.00 (dd, 1H) |
| 20 | " | —(CH₂)₃CH₃ | " | 126–127 | 1710 (KBr) | 5.79, 5.95 (dd, 1H) |
| 21 | " | —(CH₂)₄CH₃ | " | 112–114 | 1710 (KBr) | 5.80, 5.96 (dd, 1H) |
| 22 | " | —CH₂CH(CH₃)₂ | " | 137–138 | 1698 (KBr) | 5.98 (t, 1H) |
| 23 | 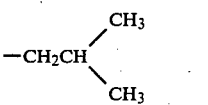 (3-CH₃-phenyl) | —(CH₂)₂CH₃ | " | 84–86 | 1708 (KBr) | 5.82, 6.00 (dd, 1H) |
| 24 | " | —(CH₂)₃CH₃ | " | 104–106 | 1708 (KBr) | 5.86, 6.04 (dd, 1H) |
| 25 | " | —(CH₂)₄CH₃ | " | 69–73 | 1710 (KBr) | 5.80, 5.97 (dd, 1H) |
| 26 | " | —CH₂CH(CH₃)₂ | " | 96–100 | 1710 (KBr) | 5.98 (t, 1H) |
| 27 | 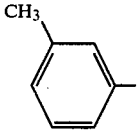 (2-CH₃-phenyl) | —(CH₂)₂CH₃ | " | 90–92 | 1710 (KBr) | 5.90, 6.06 (dd, 1H) |
| 28 | " | —(CH₂)₃CH₃ | " | 78–82 | 1710 (KBr) | 5.80, 5.95 (dd, 1H) |
| 29 | " | —(CH₂)₄CH₃ | " | 90–92 | 1710 (KBr) | 5.90, 6.07 (dd, 1H) |
| 30 | " | —CH₂CH(CH₃)₂ | " | 102–104 | 1710 (KBr) | 5.97 (t, 1H) |
| 31 | 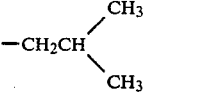 (phenyl) | —(CH₂)₃CH₃ | " | 101–102 | 1710 (KBr) | 5.90, 6.05 (dd, 1H) |
| 32 | " | —(CH₂)₄CH₃ | " | 132–133 | 1710 (KBr) | 5.75, 5.92 (dd, 1H) |

TABLE 1-continued

| Example No. | Ar | R | Acid addition salt | Melting point (°C.) | IR$_{max}$cm$^{-1}$ (C=O) | NMR ppm |
|---|---|---|---|---|---|---|
| 33 | CH₃O—⟨phenyl⟩— | —(CH₂)₃CH₃ | " | 91–93 | 1710 (KBr) | 5.70, 5.85 (dd, 1H) |
| 34 | " | —(CH₂)₄CH₃ | " | 78–80 | 1710 (KBr) | 5.70, 5.85 (dd, 1H) |

EXAMPLE 35

(a) 30 g of imidazole was dissolved in 80 ml of N,N-dimethylformamide. To this solution, 30 g of 3-bromo-2-heptanone was gradually added under stirring, and stirred at a temperature of from 50° to 60° C. for 4 hours. Then, the mixture was poured into water and extracted with chloroform. The extraction solution was treated by a usual manner, and the obtained oily product was purified by distillation, whereby 3-(imidazole-1-yl)-2-heptanone was obtained. The boiling point was 116°–119° C./2 mmHg.

(b) 2.7 g of 3-(imidazole-1-yl)-2-heptanone and 3.0 g of 3,4-dichlorobenzaldehyde were dissolved in 50 ml of methanol. While stirring this solution under cooling with ice (0°–5° C.), 2.1 g of potassium carbonate was added. Then, the mixture was stirred at the same temperature for 7 hours. The reaction mixture was poured into water and extracted with chloroform. The extraction solution was treated by a usual method, and the obtained oily product was purified by chromatography, whereby 1-(3′,4′-dichlorophenyl)-4-(imidazole-1-yl)-1-octene-3-one was obtained as an oily product.

This oily product was dissolved in 50 ml of ether, and 1 ml of concentrated nitric acid was gradually added under stirring. The precipitated crystals were collected by filtration and recrystallized from ethanolethylacetate, whereby 1-(3′,4′-dichlorophenyl)-4-(imidazole-1-yl)-1-octene-3-one nitrate was obtained.

Melting point: 119°–121° C.

IR spectrum $\nu_{maxcm-1}^{KBr}$: 2960, 2935, 1710, 1615, 1580.

NMR spectrum (δ ppm 60 Mdz, DMSO-d₆): 0.88(t, 3H), 0.9–1.7(m, 4H), 1.9–2.4 (m,2H), 5.65, 5.80(dd, 1H), 7.2–8.3(m, 8H), 9.26(m, 1H).

EXAMPLES 36 TO 88

In the same same manner as in Example 35, the following compounds were obtained starting from the corresponding (imidazole-1-yl)-ketones. The solvent for the measurement of NMR was DMSO-d₆ unless otherwise specified.

TABLE 2

| Example No. | Ar | R | Acid addition salt | Melting point (°C.) | IR$_{max}$cm$^{-1}$ (C=O) | NMR ppm |
|---|---|---|---|---|---|---|
| 36 | CH₃O—⟨phenyl⟩— | —(CH₂)₃CH₃ | | | 1710 (film) | 4.95, 5.08 (dd, 1H) (CDCl₃) |
| 37 | " | —(CH₂)₄CH₃ | Nitrate | 76–78 | 1710 (KBr) | 5.35, 5.95 (dd, 1H) |
| 38 | ⟨phenyl⟩—OCH₃ | —(CH₂)₃CH₃ | " | 93–96 | 1710 (KBr) | 5.70, 5.90 (dd, 1H) |
| 39 | " | —(CH₂)₄CH₃ | | | 1710 (film) | 4.90, 5.05 (dd, 1H) (CDCl₃) |
| 40 | CH₃O, CH₃O—⟨phenyl⟩— | —(CH₂)₃CH₃ | " | | 1710 (film) | 5.73, 5.90 (dd, 1H) |
| 41 | " | —(CH₂)₄CH₃ | " | 88–90 | 1710 (KBr) | 5.73, 5.90 (dd, 1H) |

TABLE 2-continued

| Example No. | Ar | R | Acid addition salt | Melting point (°C.) | IR$_{max}$cm$^{-1}$ (C=O) | NMR ppm |
|---|---|---|---|---|---|---|
| 42 | 2-OCH₃, 5-CH₃O phenyl | —(CH₂)₃CH₃ | " | | 1710 (film) | 5.72, 5.92 (dd, 1H) |
| 43 | " | —(CH₂)₄CH₃ | " | 78–81 | 1710 (KBr) | 5.75, 5.92 (dd, 1H) |
| 44 | 2,3-(CH₃O)₂ phenyl | —(CH₂)₃CH₃ | | | 1710 (film) | 4.98, 5.10 (dd, 1H) (CDC₃) |
| 45 | " | —(CH₂)₄CH₃ | | | 1710 (film) | 4.98, 5.13 (dd, 1H) |
| 46 | 2-OCH₃, 4-CH₃O phenyl | —(CH₂)₃CH₃ | " | 112–114 | 1710 (KBr) | 5.73, 5.91 (dd, 1H) |
| 47 | " | —(CH₂)₄CH₃ | " | 89–91 | 1710 (KBr) | 5.68, 5.85 (dd, 1H) |
| 48 | naphthalen-1-yl | —(CH₂)₃CH₃ | " | 104–106 | 1710 (KBr) | 5.95, 6.15 (dd, 1H) |
| 49 | " | —(CH₂)₄CH₃ | " | 102–104 | 1710 (KBr) | 6.09, 6.24 (dd, 1H) |
| 50 | thien-2-yl | —(CH₂)₃CH₃ | " | 138–140 | 1710 (KBr) | 5.71, 5.88 (dd, 1H) |
| 51 | 3-methylthien-2-yl | —(CH₂)₃CH₃ | " | 82–84 | 1710 (KBr) | 5.73, 5.88 (dd, 1H) |
| 52 | " | —(CH₂)₄CH₃ | " | 125–127 | 1710 (KBr) | 5.85, 6.02 (dd, 1H) |
| 53 | 5-methylthien-2-yl | —(CH₂)₃CH₃ | " | 79–81 | 1710 (KBr) | 5.80, 5.95 (dd, 1H) |
| 54 | " | —(CH₂)₄CH₃ | " | 136–138 | 1710 (KBr) | 5.78, 5.94 (dd, 1H) |
| 55 | 5-chlorothien-2-yl | —(CH₂)₃CH₃ | " | 90–93 | 1710 (KBr) | 5.72, 5.88 (dd, 1H) |
| 56 | furan-2-yl | —(CH₂)₃CH₃ | " | 115–117 | 1710 (KBr) | 5.75, 5.90 (dd, 1H) |
| 57 | " | —(CH₂)₄CH₃ | " | 127–129 | 1710 (KBr) | 5.80, 5.92 (dd, 1H) |

TABLE 2-continued

| Example No. | Ar | R | Acid addition salt | Melting point (°C.) | IR$_{max}$cm$^{-1}$ (C=O) | NMR ppm |
|---|---|---|---|---|---|---|
| 58 | 2-Cl-C$_6$H$_4$- | —(CH$_2$)$_3$CH$_3$ | " | | 1717 (film) | 5.75, 5.93 (dd, 1H) |
| 59 | " | —(CH$_2$)$_4$CH$_3$ | " | | 1717 (film) | 5.77, 5.95 (dd, 1H) |
| 60 | 3-Cl-C$_6$H$_4$- | —(CH$_2$)$_3$CH$_3$ | " | | 1710 (film) | 5.80, 5.97 (dd, 1H) |
| 61 | 2,3,4-Cl$_3$-C$_6$H$_2$- | —(CH$_2$)$_3$CH$_3$ | " | 125–127 | 1720 (KBr) | 5.82, 5.98 (dd, 1H) |
| 62 | " | —(CH$_2$)$_4$CH$_3$ | " | 106–108 | 1720 (KBr) | 5.82, 5.98 (dd, 1H) |
| 63 | 2,4-Cl$_2$-C$_6$H$_3$- | —(CH$_2$)$_3$CH$_3$ | " | | 1710 (film) | 5.75, 5.93 (dd, 1H) |
| 64 | " | —(CH$_2$)$_4$CH$_3$ | " | 89–91 | 1710 (KBr) | 5.82, 5.97 (dd, 1H) |
| 65 | 3,4-Cl$_2$-C$_6$H$_3$- | —(CH$_2$)$_4$CH$_3$ | " | | 1710 (film) | 5.80, 5.96 (dd, 1H) |
| 66 | 4-F-C$_6$H$_4$- | —(CH$_2$)$_3$CH$_3$ | " | 113–115 | 1717 (KBr) | 5.85, 6.02 (dd, 1H) |
| 67 | " | —(CH$_2$)$_4$CH$_3$ | " | 134–135 | 1717 (KBr) | 5.75, 5.93 (dd, 1H) |
| 68 | 4-(CH$_3$)$_2$N-C$_6$H$_4$- | —(CH$_2$)$_3$CH$_3$ | | 123–125 | 1690 (KBr) | 4.78, 4.90 (dd, 1H) (CDCl$_3$) |
| 69 | " | —(CH$_2$)$_4$CH$_3$ | | 93–95 | 1690 (KBr) | 4.80, 4.93 (dd, 1H) (CDCl$_3$) |
| 70 | 4-Br-C$_6$H$_4$- | —(CH$_2$)$_4$CH$_3$ | " | | 1710 (film) | 5.76, 5.95 (dd, 1H) |
| 71 | 4-CH$_3$OOC-C$_6$H$_4$- | —(CH$_2$)$_3$CH$_3$ | " | 123–124 | 1705 (KBr) | 5.82, 5.98 (dd 1H) |
| 72 | " | —(CH$_2$)$_4$CH$_3$ | " | | 1708 (film) | 5.90, 6.05 (dd, 1H) |

TABLE 2-continued

| Example No. | Ar | R | Acid addition salt | Melting point (°C.) | IR$_{max}$cm$^{-1}$ (C=O) | NMR ppm |
|---|---|---|---|---|---|---|
| 73 | CH$_3$OOC—C$_6$H$_4$— (meta) | —(CH$_2$)$_3$CH$_3$ | " | 106–107 | 1710 (KBr) | 5.88, 6.05 (dd, 1H) |
| 74 | " | —(CH$_2$)$_4$CH$_3$ | " | | 1707 (film) | 5.84, 6.00 (dd, 1H) |
| 75 | CH$_3$(CH$_2$)$_3$—C$_6$H$_4$— | —(CH$_2$)$_3$CH$_3$ | " | 101–104 | 1710 | 5.80, 5.95 (dd, 1H) |
| 76 | " | —(CH$_2$)$_4$CH$_3$ | " | 95–97 | 1710 (KBr) | 5.80, 5.95 (dd, 1H) |
| 77 | CH$_3$CH$_2$CH(CH$_3$)—C$_6$H$_4$— | —(CH$_2$)$_3$CH$_3$ | " | 101–102 | 1710 (KBr) | 5.85, 6.02 (dd, 1H) |
| 78 | " | —(CH$_2$)$_4$CH$_3$ | | | 1710 (film) | 4.92, 5.05 (dd, 1H) (CDCl$_3$) |
| 79 | (CH$_3$)$_3$C—C$_6$H$_4$— | —(CH$_2$)$_3$CH$_3$ | " | | 1712 (film) | 5.78, 5.84 (dd, 1H) |
| 80 | " | —(CH$_2$)$_4$CH$_3$ | " | | 1710 (film) | 5.85, 6.02 (dd, 1H) |
| 81 | C$_6$H$_5$—C$_6$H$_4$— | —(CH$_2$)$_3$CH$_3$ | | 145–146 | 1710 (KBr) | 4.81, 4.96 (dd, 1H) (CDCl$_3$) |
| 82 | " | —(CH$_2$)$_4$CH$_3$ | | 133–134 | 1715 (KBr) | 4.81, 4.96 (dd, 1H) (CDCl$_3$) |
| 83 | HO—C$_6$H$_4$— | —(CH$_2$)$_3$CH$_3$ | | 163–166 | 1702 (KBr) | 5.30, 5.45 (dd, 1H) |
| 84 | " | —(CH$_2$)$_4$CH$_3$ | | 177–179 | 1706 (KBr) | 5.28, 5.45 (dd, 1H) |
| 85 | 3,4-(HO)$_2$—C$_6$H$_3$— | —(CH$_2$)$_3$CH$_3$ | | 84–90 | 1710 (KBr) | 5.32, 5.45 (dd, 1H) |
| 86 | " | —(CH$_2$)$_4$CH$_3$ | | 130–135 | 1710 (KBr) | 5.29, 5.44 (dd, 1H) |
| 87 | 3-CH$_3$O-4-HO—C$_6$H$_3$— | —(CH$_2$)$_3$CH$_3$ | | 127–129 | 1710 (KBr) | 5.28, 5.44 (dd, 1H) |
| 88 | " | —(CH$_2$)$_4$CH$_3$ | | 140–143 | 1710 (KBr) | 5.35, 5.50 (dd, 1H) |

TEST EXAMPLE 1

Tests for Bacteriostatic and Fungistatic Activities

With respect to various bacteria and fungi, the bacteriostatic and fungistatic activities were measured by a plate dilution method. In the case of bacteria, the measurements were conducted after culturing them at 37° C. for 2 days by means of a bouillon agar culture medium. In the case of fungi, the measurements were conducted after culturing then by means of Sabouraud agar culture medium at 37° C. for 2 days in the case of Candida and at 27° C. for 7 days in the case of Trichophyton. The results thereby obtained are shown in Table 3. The numerical values represent the minimum growth inhibition concentrations. From the results of the tests, it is evident that the products of the present invention exhibit superior antifungal activities. In Comparative Example 1, phenyl 11-iodo-10-undecynoate was used. Likewise, in Comparative Example 2, miconazole was used.

Phenyl 11-iodo-10-undecynoate:

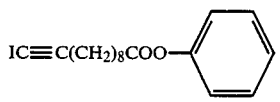

Miconazole:

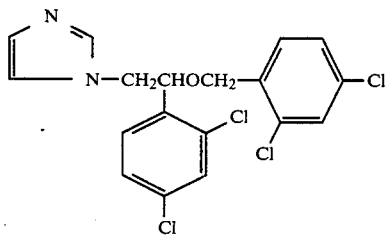

TABLE 3

| Example No. | Trichophyton mentagrophytes | Trichophyton rubrum | Candida albicans | Cryptococcus neoformans | Staphylococcus aureus |
| --- | --- | --- | --- | --- | --- |
| 1 | 1.56 | 0.2 | 12.5 | 0.1 | 1.56 |
| 2 | 3.13 | 0.78 | 12.5 | 0.39 | 3.13 |
| 3 | 1.56 | 0.39 | 6.25 | 0.2 | 3.13 |
| 4 | 1.56 | 0.39 | 12.5 | 0.1 | 1.56 |
| 5 | 3.13 | 0.39 | 3.13 | 0.1 | 1.56 |
| 9 | 1.56 | 0.2 | 6.25 | 0.39 | 3.13 |
| 10 | 1.56 | 0.2 | 3.13 | 0.2 | 1.56 |
| 11 | 1.56 | 0.39 | 12.5 | 0.78 | 3.13 |
| 12 | 1.56 | 0.39 | 6.25 | 0.39 | 1.56 |
| 13 | 3.13 | 0.39 | 6.25 | 0.39 | 3.13 |
| 19 | 3.13 | 0.39 | 1.56 | 0.39 | 6.25 |
| 20 | 3.13 | 0.39 | 3.13 | 0.2 | 6.25 |
| 21 | 6.25 | 0.39 | 3.13 | 0.39 | 6.25 |
| 34 | 6.25 | 0.39 | 12.5 | 0.78 | 3.13 |
| 35 | 1.56 | 0.39 | 12.5 | 0.2 | 1.56 |
| 53 | 3.13 | 1.56 | 12.5 | 0.39 | 3.13 |
| 55 | 3.13 | 1.56 | 12.5 | 0.39 | 3.13 |
| 63 | 1.56 | 1.56 | 12.5 | 0.39 | 6.25 |
| 65 | 3.13 | 0.78 | 12.5 | 0.2 | 3.13 |
| 70 | 3.13 | 0.2 | 12.5 | 1.56 | 6.25 |
| 71 | 3.13 | 0.78 | 25 | 1.56 | 6.25 |
| Comparative Example 1 | 12.5 | 25 | 25 | 6.25 | 100 |
| Comparative Example 2 | 6.25 | 0.39 | 25 | 0.78 | 0.78 |

TEST EXAMPLE 2

Tests for Antitrichophytosis Activities

The tests were conducted in accordance with a Kaken method (see The Japanese Journal of Medical Mycology, Vol. 1, p 252 (1960)). Four portions on the back of a Hartly guinea pig (weight: 600-700 g) were depilated for 4 cm² each, mildly scratched with a sand paper, and then infected with the second generation of Trichophyton mentagrophytes cultured in a guinea pig at a rate of $1\times 10^5$ spores per infected portion. From 48 hours after the infection, 0.2 ml of a test sample dissolved in ethanol was applied once a day for 10 times. After 2 days from the final treatment, the guinea pig was killed, and 10 culture tissues from each infected portion were taken and placed on a Sabouraud agar plate containing cyclohexamine and kanamycin and cultured at 27° C. for 7 days, whereupon the presence or absence or Trichophyton was determined. The inhibition rate was obtained in accordance with the following equation. The test results are shown in Table 4.

$$\text{Inhibition rate} = \left(1 - \frac{\text{Number of positive culture tissues}}{\text{Total number of culture tissues}}\right) \times 100$$

TABLE 4

| Example No. | Concentration (%) | Number of animals | Number of positive culture tissues | Total number of culture tissues | Inhibition rate (%) |
| --- | --- | --- | --- | --- | --- |
| Contrast | | 10 | 100 | 100 | 0 |
| Ethanol | | 5 | 50 | 50 | 0 |
| 1 | 1.0 | 5 | 5 | 50 | 90 |
| 3 | 1.0 | 5 | 4 | 50 | 92 |
| 4 | 1.0 | 5 | 5 | 50 | 90 |
| 5 | 1.0 | 5 | 11 | 50 | 78 |
| 9 | 1.0 | 5 | 13 | 50 | 74 |
| 10 | 1.0 | 5 | 12 | 50 | 76 |
| 11 | 1.0 | 5 | 15 | 50 | 70 |
| 12 | 1.0 | 5 | 7 | 50 | 86 |
| 13 | 1.0 | 5 | 11 | 50 | 78 |
| 35 | 1.0 | 5 | 9 | 50 | 82 |
| 63 | 1.0 | 5 | 18 | 50 | 64 |
| Comparative Example 1 | 1.0 | 5 | 13 | 50 | 74 |
| Comparative Example 2 | 1.0 | 5 | 15 | 50 | 70 |

TEST EXAMPLE 3

Acute Toxicity

A suspension of a sample in a 0.5% methylcellulose 50 was administered i.p. to jcl:ICR female mice of 5 weeks old. $LD_{50}$ was calculated from the mortality after 7 days from the date of the administration. As a result, $LD_{50}$ of the compound of Example 4 was found to be about 250 mg/kg.

We claim:

1. An imidazole derivative represented by formula I or a biologically acceptable acid addition salt thereof:

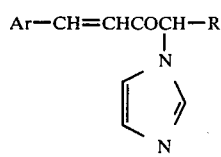

where Ar is a phenyl group which may be substituted by alkyl having from 1 to 6 carbon atoms, alkoxy having from 1 to 4 carbon atoms, alkylamino having from 1 to 4 carbon atoms, alkoxy carbonyl having from 1 to 4 carbon atoms, phenyl, halogen or hydroxyl; a naphthyl group; a furyl group; or a thienyl group which may be substituted by halogen or alkyl having from 1 to 4 carbon atoms, and R is an alkyl group having from 1 to 10 carbon atoms; an alkenyl group having from 1 to 6 carbon atoms; or a phenylalkyl group which may be substituted by halogen.

2. The imidazole derivative of the formula I or a biologically acceptable acid addition salt thereof according to claim 1, wherein Ar is

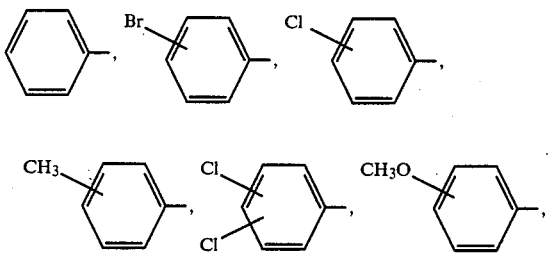

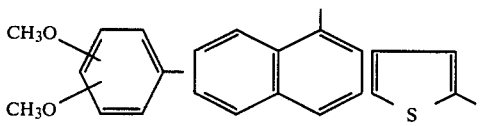

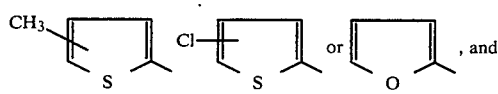

R is —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —CH(CH$_3$)$_2$, —CH$_2$CH(CH$_3$)$_2$, —CH$_2$CH=CH$_2$, —CH$_2$CH=CHCH$_3$, —CH$_2$CH=C(CH$_3$)$_2$,

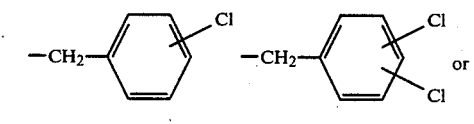

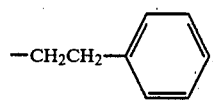

3. 1-(4'-Bromophenyl)-4-(imidazole-1-yl)-1-octene-3-one or a biologically acceptable acid addition salt thereof according to claim 1.

4. 1-(4'-Chlorophenyl)-4-(imidazole-1-yl)-1-hexene-3-one or a biologically acceptable acid addition salt thereof according to claim 1.

5. 1-(4'-Chlorophenyl)-4-(imidazole-1-yl)-1-heptene-3-one or a biologically acceptable acid addition salt thereof according to claim 1.

6. 1-(4'-Chlorophenyl)-4-(imidazole-1-yl)-1-octene-3-one or a biologically acceptable acid addition salt thereof according to claim 1.

7. 1-(4'-Chlorophenyl)-4-(imidazole-1-yl)-1-nonene-3-one or a biologically acceptable acid addition salt thereof according to claim 1.

* * * * *